(12) United States Patent
Richelsoph (10) Patent No.: US 9,456,851 B2
(45) Date of Patent: Oct. 4, 2016

(54) SPINAL IMPLANT

(75) Inventor: Marc Richelsoph, Charlotte, NC (US)

(73) Assignee: Intelligent Implant Systems, LLC, Charlotte, NC (US)

( * ) Notice: Subject to any disclaimer, the term of this patent is extended or adjusted under 35 U.S.C. 154(b) by 62 days.

(21) Appl. No.: 13/045,478

(22) Filed: Mar. 10, 2011

(65) Prior Publication Data

US 2011/0213419 A1    Sep. 1, 2011

Related U.S. Application Data

(63) Continuation of application No. 11/876,890, filed on Oct. 23, 2007, now abandoned.

(51) Int. Cl.
*A61B 17/70* (2006.01)
(52) U.S. Cl.
CPC ....... *A61B 17/7035* (2013.01); *A61B 17/7032* (2013.01); *A61B 17/7037* (2013.01)
(58) Field of Classification Search
CPC .......... A61B 17/7032; A61B 17/7034; A61B 17/7035; A61B 17/7037
USPC .................................. 606/246–279, 300–321
See application file for complete search history.

(56) References Cited

U.S. PATENT DOCUMENTS

| | | | |
|---|---|---|---|
| 2,855,232 A | 10/1958 | Kozak | |
| 3,599,245 A | 8/1971 | Blatchford | |
| 3,997,138 A | 12/1976 | Crock et al. | |
| 4,041,939 A | 8/1977 | Hall | |
| 4,269,178 A | 5/1981 | Keene | |
| 4,404,967 A | 9/1983 | Bacal et al. | |
| 4,411,259 A | 10/1983 | Drummond | |
| 4,419,026 A | 12/1983 | Leto | |
| 4,611,581 A | 9/1986 | Steffee | |
| 4,706,367 A | 11/1987 | Garringer | |

(Continued)

FOREIGN PATENT DOCUMENTS

| | | |
|---|---|---|
| WO | 97/02786 | 1/1997 |
| WO | 00/18310 | 4/2000 |

(Continued)

OTHER PUBLICATIONS

European Search Report of European App. No. 12 16 7524 dated Jan. 31, 2013.

(Continued)

*Primary Examiner* — Ellen C Hammond
*Assistant Examiner* — Christina Negrellirodrigue
(74) *Attorney, Agent, or Firm* — Mayback & Hoffman, P.A.; Gregory L. Mayback (57) ABSTRACT

A screw and rod fixation assembly includes a body member including a screw seat for seating a screw head therein and a rod seat for seating a rod therein. An adjustable locking ring applies a locking force against the screw head seated in the screw seat and a locking cap adjustably applies a locking force against a rod seated in the rod seat. The adjustable screw locking ring and locking cap function independent of each other.

A method of fixing the rod to the screw includes the steps of inserting a screw head into a screw seat in one end of a body member and inserting a rod into a rod seat in a second end of a body member and selectively and independently adjusting a locking force on both the screw head and the rod within the screw seat and rod seat, respectively.

13 Claims, 11 Drawing Sheets

(56) References Cited

U.S. PATENT DOCUMENTS

| | | | |
|---|---|---|---|
| 4,836,196 A | 6/1989 | Park et al. | |
| 4,887,595 A | 12/1989 | Heinig et al. | |
| 4,946,458 A * | 8/1990 | Harms | A61B 17/7002 606/264 |
| 4,947,835 A | 8/1990 | Hepburn et al. | |
| 4,950,269 A * | 8/1990 | Gaines, Jr. | 606/261 |
| 5,010,879 A | 4/1991 | Moriya et al. | |
| 5,036,837 A | 8/1991 | Mitchell et al. | |
| 5,084,048 A | 1/1992 | Jacob et al. | |
| 5,122,131 A | 6/1992 | Tsou | |
| 5,129,899 A | 7/1992 | Small et al. | |
| 5,176,679 A | 1/1993 | Lin | |
| 5,201,734 A | 4/1993 | Cozad et al. | |
| 5,261,913 A * | 11/1993 | Marnay | 606/251 |
| 5,281,222 A | 1/1994 | Allard et al. | |
| 5,356,411 A | 10/1994 | Spievack | |
| 5,380,325 A | 1/1995 | Lahille et al. | |
| 5,395,371 A | 3/1995 | Miller et al. | |
| 5,443,467 A * | 8/1995 | Biedermann et al. | 606/65 |
| 5,474,551 A * | 12/1995 | Finn et al. | 606/264 |
| 5,476,462 A | 12/1995 | Allard et al. | |
| 5,501,684 A | 3/1996 | Schlapfer et al. | |
| 5,507,746 A | 4/1996 | Lin | |
| 5,516,335 A | 5/1996 | Kummer et al. | |
| 5,531,745 A | 7/1996 | Ray | |
| 5,531,747 A | 7/1996 | Ray | |
| 5,540,690 A | 7/1996 | Miller et al. | |
| 5,545,163 A | 8/1996 | Miller et al. | |
| 5,549,608 A * | 8/1996 | Errico | A61B 17/7055 606/264 |
| 5,562,660 A | 10/1996 | Grob | |
| 5,575,792 A * | 11/1996 | Errico et al. | 606/276 |
| 5,578,033 A * | 11/1996 | Errico et al. | 606/276 |
| 5,584,834 A | 12/1996 | Errico | |
| 5,586,984 A * | 12/1996 | Errico et al. | 606/264 |
| 5,591,165 A | 1/1997 | Jackson | |
| 5,630,817 A | 5/1997 | Rokegem et al. | |
| 5,716,356 A | 2/1998 | Biedermann et al. | |
| 5,728,098 A * | 3/1998 | Sherman | A61B 17/7032 606/269 |
| 5,733,284 A | 3/1998 | Martin | |
| 5,733,285 A | 3/1998 | Errico et al. | |
| 5,879,350 A | 3/1999 | Sherman et al. | |
| 5,882,350 A | 3/1999 | Ralph et al. | |
| 5,891,145 A | 4/1999 | Morrison | |
| 5,954,725 A * | 9/1999 | Sherman et al. | 606/78 |
| 5,984,928 A | 11/1999 | Hermann | |
| 6,022,350 A | 2/2000 | Ganem | |
| 6,045,552 A | 4/2000 | Zucherman et al. | |
| 6,063,090 A | 5/2000 | Schlapfer | |
| 6,113,601 A | 9/2000 | Tatar | |
| 6,132,432 A | 10/2000 | Richelsoph | |
| 6,206,879 B1 | 3/2001 | Marnay et al. | |
| 6,248,105 B1 | 6/2001 | Schlapfer et al. | |
| 6,254,602 B1 * | 7/2001 | Justis | A61B 17/7032 606/272 |
| 6,273,888 B1 * | 8/2001 | Justis | A61B 17/7032 606/272 |
| 6,290,703 B1 | 9/2001 | Ganem | |
| 6,302,888 B1 | 10/2001 | Mellinger et al. | |
| 6,355,040 B1 | 3/2002 | Richelsoph et al. | |
| 6,379,354 B1 | 4/2002 | Rogozinski | |
| 6,554,834 B1 * | 4/2003 | Crozet et al. | 606/65 |
| 6,582,400 B1 | 6/2003 | Hawk et al. | |
| 6,585,737 B1 | 7/2003 | Braccelli et al. | |
| 6,623,485 B2 | 9/2003 | Doubler et al. | |
| 6,626,904 B1 | 9/2003 | Jammet et al. | |
| 6,641,586 B2 * | 11/2003 | Varieur | 606/270 |
| 6,755,829 B1 | 6/2004 | Bono et al. | |
| 6,770,094 B2 | 8/2004 | Fehling et al. | |
| 6,843,791 B2 | 1/2005 | Serhan | |
| 6,911,030 B1 * | 6/2005 | Vanacker et al. | 606/270 |
| 6,964,666 B2 | 11/2005 | Jackson | |
| 7,163,539 B2 | 1/2007 | Abdelgany | |
| 7,186,255 B2 | 3/2007 | Baynham | |
| 7,207,992 B2 | 4/2007 | Ritland | |
| 7,326,210 B2 | 2/2008 | Jahng et al. | |
| 7,591,839 B2 | 9/2009 | Biedermann et al. | |
| 7,686,833 B1 | 3/2010 | Muhanna et al. | |
| 7,736,380 B2 | 6/2010 | Johnston et al. | |
| 7,803,174 B2 | 9/2010 | Denis et al. | |
| 7,806,913 B2 | 10/2010 | Fanger et al. | |
| 7,867,255 B2 | 1/2011 | Miller et al. | |
| 7,931,675 B2 | 4/2011 | Panjabi et al. | |
| 7,935,134 B2 | 5/2011 | Reglos et al. | |
| 7,935,137 B2 | 5/2011 | Gorhan et al. | |
| 7,981,141 B2 | 7/2011 | Morrison et al. | |
| 7,981,142 B2 | 7/2011 | Konieczynski et al. | |
| 8,002,806 B2 * | 8/2011 | Justis | A61B 17/7038 606/246 |
| 8,002,808 B2 | 8/2011 | Morrison et al. | |
| 8,007,523 B2 | 8/2011 | Wagner et al. | |
| 8,012,188 B2 | 9/2011 | Melkent et al. | |
| 8,048,123 B2 | 11/2011 | Mitchell et al. | |
| 8,062,338 B2 | 11/2011 | McBride et al. | |
| 8,062,341 B2 | 11/2011 | Binder et al. | |
| 8,062,367 B2 | 11/2011 | Kirschman | |
| 8,092,498 B2 * | 1/2012 | Samudrala et al. | 606/250 |
| 8,092,501 B2 | 1/2012 | Mitchell et al. | |
| 8,172,885 B2 | 5/2012 | Songer et al. | |
| 8,197,519 B2 * | 6/2012 | Schlaepfer | A61B 17/7034 606/278 |
| 8,216,285 B2 | 7/2012 | Markworth | |
| 8,221,476 B2 | 7/2012 | Paul | |
| 8,236,033 B2 | 8/2012 | Paul | |
| 8,236,034 B2 | 8/2012 | Binder et al. | |
| 8,262,708 B2 | 9/2012 | Michelson | |
| 8,277,493 B2 | 10/2012 | Farris et al. | |
| 8,323,283 B2 | 12/2012 | Michelson | |
| 8,348,982 B2 | 1/2013 | Baynham et al. | |
| 8,361,125 B2 | 1/2013 | Taylor et al. | |
| 8,361,126 B2 | 1/2013 | Perrow et al. | |
| 8,361,129 B2 * | 1/2013 | Chao | A61B 17/7037 606/264 |
| 8,372,152 B2 | 2/2013 | Kirschman | |
| 8,382,809 B2 | 2/2013 | Kaufman et al. | |
| 8,403,970 B1 | 3/2013 | Bedor | |
| 8,403,971 B2 | 3/2013 | Barrus et al. | |
| 8,409,259 B1 | 4/2013 | Bedor | |
| 8,409,260 B2 | 4/2013 | Biedermann et al. | |
| 8,425,514 B2 | 4/2013 | Anderson et al. | |
| 8,425,576 B2 | 4/2013 | Anderson et al. | |
| 8,435,266 B2 | 5/2013 | Richelsoph | |
| 8,439,923 B2 | 5/2013 | Won et al. | |
| 8,480,716 B2 | 7/2013 | Perrow et al. | |
| 8,652,176 B2 | 2/2014 | Ramadan et al. | |
| 8,652,178 B2 | 2/2014 | Abelgany | |
| 8,672,978 B2 | 3/2014 | Dant et al. | |
| 8,672,984 B2 | 3/2014 | Lindemann et al. | |
| 8,764,804 B2 | 7/2014 | Rezach | |
| 8,771,319 B2 | 7/2014 | Prajapati | |
| 8,795,340 B2 | 8/2014 | Weiman | |
| 8,840,649 B2 | 9/2014 | de Coninck | |
| 2001/0012937 A1 | 8/2001 | Schaffler-Wachter et al. | |
| 2001/0047173 A1 | 11/2001 | Schlapfer et al. | |
| 2002/0032443 A1 | 3/2002 | Sherman et al. | |
| 2002/0052603 A1 | 5/2002 | Nichols et al. | |
| 2003/0023240 A1 | 1/2003 | Amrein et al. | |
| 2003/0023243 A1 | 1/2003 | Biedermann et al. | |
| 2003/0093078 A1 | 5/2003 | Ritland | |
| 2003/0216735 A1 | 11/2003 | Altarac | |
| 2004/0049190 A1 | 3/2004 | Biedermann et al. | |
| 2004/0097933 A1 | 5/2004 | Lourdel et al. | |
| 2004/0127899 A1 | 7/2004 | Konieczynski et al. | |
| 2004/0143264 A1 | 7/2004 | McAfee | |
| 2004/0225289 A1 | 11/2004 | Biedermann et al. | |
| 2004/0260284 A1 * | 12/2004 | Parker | 606/61 |
| 2005/0080415 A1 * | 4/2005 | Keyer | A61B 17/7038 606/278 |
| 2005/0085812 A1 | 4/2005 | Sherman et al. | |
| 2005/0096653 A1 | 5/2005 | Doubler et al. | |
| 2005/0143737 A1 | 6/2005 | Pafford et al. | |
| 2005/0171537 A1 | 8/2005 | Mazel et al. | |
| 2005/0171542 A1 | 8/2005 | Biedermann et al. | |

(56) References Cited

U.S. PATENT DOCUMENTS

| | | |
|---|---|---|
| 2005/0203516 A1 | 9/2005 | Biedermann |
| 2005/0203517 A1 | 9/2005 | Jahng et al. |
| 2005/0215001 A1 | 9/2005 | David |
| 2005/0216003 A1 | 9/2005 | Biedermann et al. |
| 2005/0222570 A1 | 10/2005 | Jackson |
| 2005/0228379 A1 | 10/2005 | Jackson |
| 2005/0261687 A1 | 11/2005 | Garamszegi |
| 2005/0267472 A1 | 12/2005 | Biedermann et al. |
| 2005/0267485 A1 | 12/2005 | Cordes et al. |
| 2005/0277924 A1 | 12/2005 | Roychowdhury |
| 2005/0277927 A1 | 12/2005 | Guenther |
| 2006/0004357 A1* | 1/2006 | Lee et al. .................. 606/61 |
| 2006/0009767 A1 | 1/2006 | Kiester |
| 2006/0036240 A1 | 2/2006 | Colleran et al. |
| 2006/0036242 A1 | 2/2006 | Nilsson |
| 2006/0036252 A1* | 2/2006 | Baynham et al. ............ 606/73 |
| 2006/0058788 A1 | 3/2006 | Hammer |
| 2006/0058789 A1 | 3/2006 | Kim et al. |
| 2006/0074419 A1 | 4/2006 | Taylor et al. |
| 2006/0084979 A1 | 4/2006 | Jackson |
| 2006/0095038 A1 | 5/2006 | Jackson |
| 2006/0100621 A1 | 5/2006 | Jackson |
| 2006/0100622 A1 | 5/2006 | Jackson |
| 2006/0149233 A1 | 7/2006 | Richelsoph |
| 2006/0149240 A1 | 7/2006 | Jackson |
| 2006/0149241 A1 | 7/2006 | Richelsoph |
| 2006/0155279 A1 | 7/2006 | Ogilvie |
| 2006/0161152 A1 | 7/2006 | Ensign et al. |
| 2006/0173456 A1 | 8/2006 | Hawkes et al. |
| 2006/0200133 A1 | 9/2006 | Jackson |
| 2006/0200147 A1 | 9/2006 | Ensign et al. |
| 2006/0229606 A1 | 10/2006 | Clement et al. |
| 2006/0233597 A1 | 10/2006 | Ensign et al. |
| 2006/0235385 A1 | 10/2006 | Whipple |
| 2006/0235392 A1 | 10/2006 | Hammer |
| 2006/0235393 A1 | 10/2006 | Bono |
| 2006/0241594 A1 | 10/2006 | McCarthy et al. |
| 2006/0241599 A1 | 10/2006 | Konieczynski |
| 2006/0241603 A1 | 10/2006 | Jackson |
| 2006/0247635 A1 | 11/2006 | Gordon et al. |
| 2006/0264937 A1 | 11/2006 | White |
| 2006/0265074 A1 | 11/2006 | Krishna et al. |
| 2006/0271047 A1 | 11/2006 | Jackson |
| 2006/0276789 A1 | 12/2006 | Jackson |
| 2006/0276792 A1* | 12/2006 | Ensign ............... A61B 17/7037 606/264 |
| 2007/0010817 A1 | 1/2007 | de Coninck |
| 2007/0016204 A1 | 1/2007 | Martinez et al. |
| 2007/0055235 A1 | 3/2007 | Janowski |
| 2007/0055242 A1 | 3/2007 | Bailly |
| 2007/0093817 A1* | 4/2007 | Barrus ............... A61B 17/7032 606/264 |
| 2007/0093820 A1 | 4/2007 | Freudiger et al. |
| 2007/0093832 A1 | 4/2007 | Abdelgany |
| 2007/0118122 A1 | 5/2007 | Butler et al. |
| 2007/0118123 A1 | 5/2007 | Strausbaugh |
| 2007/0123867 A1 | 5/2007 | Kirschman |
| 2007/0157543 A1 | 7/2007 | Metz-Stavenhagen |
| 2007/0161999 A1 | 7/2007 | Biedermann |
| 2007/0167948 A1 | 7/2007 | Abdou |
| 2007/0167949 A1 | 7/2007 | Altarac |
| 2007/0173817 A1 | 7/2007 | Sournac et al. |
| 2007/0173818 A1 | 7/2007 | Hestad et al. |
| 2007/0173819 A1 | 7/2007 | Sandlin |
| 2007/0173833 A1 | 7/2007 | Butler |
| 2007/0225707 A1 | 9/2007 | Wisnewski et al. |
| 2007/0233080 A1 | 10/2007 | Na et al. |
| 2007/0233086 A1 | 10/2007 | Harms |
| 2007/0233087 A1 | 10/2007 | Schlapfer |
| 2007/0239159 A1 | 10/2007 | Altarac et al. |
| 2007/0270818 A1 | 11/2007 | Rezach |
| 2008/0015588 A1 | 1/2008 | Hawkes |
| 2008/0027436 A1 | 1/2008 | Cournoyer et al. |
| 2008/0077139 A1 | 3/2008 | Landry et al. |
| 2008/0119853 A1 | 5/2008 | Felt et al. |
| 2008/0172093 A1 | 7/2008 | Nilsson |
| 2008/0177321 A1 | 7/2008 | Drewry |
| 2008/0183212 A1 | 7/2008 | Veldman et al. |
| 2008/0183213 A1 | 7/2008 | Veldman et al. |
| 2008/0195153 A1 | 8/2008 | Thompson |
| 2008/0195159 A1 | 8/2008 | Kloss et al. |
| 2008/0208260 A1 | 8/2008 | Truckai et al. |
| 2008/0243189 A1 | 10/2008 | Purcell et al. |
| 2008/0262553 A1 | 10/2008 | Hawkins et al. |
| 2009/0093820 A1 | 4/2009 | Trieu et al. |
| 2009/0204155 A1 | 8/2009 | Aschmann |
| 2009/0204156 A1 | 8/2009 | McClintock et al. |
| 2009/0248088 A1 | 10/2009 | Biedermann |
| 2009/0254123 A1 | 10/2009 | Pafford et al. |
| 2009/0287260 A1 | 11/2009 | Zehnder |
| 2009/0326584 A1 | 12/2009 | Slivka et al. |
| 2010/0036423 A1 | 2/2010 | Hayes et al. |
| 2010/0057126 A1 | 3/2010 | Hestad |
| 2010/0063551 A1 | 3/2010 | Richelsoph |
| 2010/0087865 A1 | 4/2010 | Biedermann et al. |
| 2010/0114318 A1 | 5/2010 | Gittings et al. |
| 2010/0137913 A1 | 6/2010 | Khatchadourian et al. |
| 2010/0185247 A1 | 7/2010 | Richelsoph |
| 2010/0217319 A1 | 8/2010 | Todd |
| 2010/0331884 A1 | 12/2010 | Hestad |
| 2010/0331886 A1 | 12/2010 | Fanger et al. |
| 2011/0004251 A1 | 1/2011 | Sweeney et al. |
| 2011/0077691 A1 | 3/2011 | de Coninck |
| 2011/0196423 A1 | 8/2011 | Ziolo et al. |
| 2011/0230916 A1 | 9/2011 | Richelsoph |
| 2011/0245873 A1 | 10/2011 | Winslow et al. |
| 2011/0270314 A1 | 11/2011 | Mueller et al. |
| 2012/0130427 A1 | 5/2012 | Hoffman et al. |
| 2014/0228895 A1 | 8/2014 | Ziolo et al. |

FOREIGN PATENT DOCUMENTS

| | | |
|---|---|---|
| WO | 2005074823 A1 | 8/2005 |
| WO | 2006060430 | 6/2006 |
| WO | 2006065607 | 6/2006 |
| WO | 2007082019 | 7/2007 |
| WO | 2008078163 A2 | 7/2008 |

OTHER PUBLICATIONS

International Search Report and Written Opinion of the International Searching Authority, Issued Jan. 16, 2015 by the International Searching Authority, in reference to PCT Application No. PCT/US2014/059475.

Stryker, Techtonix Surgical Protocol, Stryker Spine, Literature No. TLTCTSTIA, Feb. 2006, Allendale, New Jersey.

Supplementary European Search Report of European Patent App. No. 09 81 3525 dated Feb. 6, 2013.

International Search Report of PCT App. No. PCT/US2009/056343 dated Nov. 25, 2009.

Japanese Notification of Reasons for Refusal for Japanese Patent Application No. 2011-526300 dated Sep. 9, 2013.

Japanese Notification of Reasons for Refusal, Final, for Japanese Patent Application No. 2011-526300 dated Aug. 4, 2014.

* cited by examiner

SPINAL IMPLANT

RELATED APPLICATION

This application is a continuation application of U.S. application Ser. No. 11/876,890 which was filed Oct. 23, 2007, the contents of which are incorporated herein by reference as if set forth in full.

TECHNICAL FIELD

The present invention generally relates to spinal implants. More particularly, the present invention relates to screw fixation assemblies for use with bone fixation systems.

BACKGROUND ART

Polyaxial screw implants for assisting in fusion surgeries have been in use for many years. Typically, polyaxial screw motion implants allow motion of a body portion around a spherical screw head to allow the assembly to pivot. When individual screw assemblies are connected by a rod, it is common for the rod to be out of alignment with all of the screw assemblies. This problem increases in severity with an increasing number of screw assemblies that the surgeon is trying to connect to the same rod. Pivoting allows the assembly to compensate for this problem.

The main problems with polyaxial screws are package size and implant locking. Most implants are fairly large in size in order to allow enough force to be exerted against the spherical screw head and rod without the implant flexing under the load. For all of these implants, and a few that are small in size, the locking component is complex and often involves the use of threads. Set screws and threaded nuts are commonly used. Finding a thread inside the implantation site is difficult and creates issues such as cross-threading. Other concepts have been invented, but as a combination of effective locking and small package size, room for improvement exists.

In the majority of the prior art screw assemblies, the screw head portion of the screw is spherical in form, such that it can rotate in all directions. There are a few exceptions to the rule, but the result is essentially the same. For example, U.S. Pat. No. 7,186,255 to Baynham et al. shows a screw portion having a spherical head separated from the screw shank. However, once assembled, the screw is no different than the other prior art. U.S. Pat. No. 7,163,539 to Abdelgany et al. shows a screw with a partial spherical head that has been hollowed. However, the concept is still providing a spherical head. This approach also has limitations in the amount of allowable rotation in all directions, as the edges of the head contact the rod when the head is rotated. U.S. Pat. No. 5,891,145 to Morrison et al. utilizes a polyaxial screw head with a disk-like projection resting in a taper. This complex design requires compression of the disk-like projection in a taper. The difficulties in this are high because when the screw head rotates, only a small portion of the disk-like projection is in contact with the taper, thereby making it almost impossible to lock the angulation of the screw in position.

U.S. Pat. No. 5,584,834 to Errico et al. discloses that a taper is required on the exterior surface of an external ring to engage and create sufficient pressure to lock a screw head. In addition, this design is restricted to a curvate screw head. The external locking collar is also tapered on its inside aspect and it is a requirement of the design. U.S. Pat. No. 5,578,033 to Errico et al. discloses a spherical head of a hook that is used in place of a spherical head of a screw. The implant loads the rod component from the side, with a locking collar sliding over a tapered lower section. Both of these prior art Errico patents require the use of a locking nut to lock the assembly in its final position. U.S. Pat. No. 5,586,984 to Errico et al. discloses an external taper on a body portion of a locking ring to clamp the tapered section against a round screw head. This is also done by advancing a threaded nut.

United States Publication No. 2007/0173819 to Sandlin et al. shows a locking cap design to engage a tapered upper portion of a body. A tapered portion can be used to cause contouring around a rod, which has been shown in other prior art patents. The cap also engages in such a way as to be fully locked or not locked at all. There are no provisions for partial locking.

SUMMARY OF THE INVENTION

According to the present invention, there is provided a screw and rod fixation assembly comprising a body member including a screw seat for seating a screw head therein and a rod seat for seating a rod therein. Adjustable rod locking means adjustably applies a locking force against a rod seated in the rod seat. An adjustable screw locking means adjustably applies a locking force to a screw head seated in the screw seat. The adjustable screw locking means is functionally independent of the adjustable rod locking means.

The present invention further provides a screw and rod fixation member including a body portion having a first end having a screw seat for seating a screw head therein and a second end including a rod seat for seating a rod therein. The first end includes a pocket therein having outwardly flexible walls for receiving a screw head therein, thereby defining a screw seat. The second end includes a base portion and two spaced arms extending therefrom defining a rod seat. The arms include a smooth outer surface and fixing means for engagement with a rod locking member.

The present invention also provides a fixation screw including a threaded portion for engagement with a bone and a head portion and a neck portion therebetween. The screw head includes multiple engagement surfaces for contacting multiple areas of a spherical screw seat surface.

The present invention provides a method of fixing a rod to a screw by inserting a screw head into a screw seat in one end of a body member and inserting a rod into a rod seat in a second end of the body member. A locking force is selectively and independently adjusted on both the screw head and the rod within the screw seat and rod seat, respectively.

In addition, the present invention further provides a method of fixing a rod to a screw head by seating a screw head having multiple contact points in a screw seat of a body portion causing the screw head to interfere with and contact multiple portions of the spherical seat creating sufficient friction to lock the screw head in a desired position during rod insertion while allowing the body portion to rotate relative to the screw head.

DESCRIPTION OF THE DRAWINGS

Other advantages of the present invention are readily appreciated as the same becomes better understood by reference to the following detailed description when considered in connection with the accompanying drawings wherein.

DETAILED DESCRIPTION OF THE INVENTION

In accordance with the present invention, a screw and rod fixation assembly is generally shown at 10 in the figures. Most generally, the assembly includes a body member 100 including a screw seat 119 for seating a screw head therein and a rod seat 116 for seating a rod 104 therein. An adjustable rod locking mechanism in the form of a rod locking member 102 adjustably applies a locking force against a rod 104 seated in the rod seat 116. An adjustable screw locking mechanism in the form of a screw locking ring 101 adjustably applies a locking force to a screw head seated in the screw seat 119. The adjustable screw locking mechanism is functionally independent of the adjustable rod locking mechanism. Thus, in use, a practicing physician can independently adjust the body member relative to the screw and, independently, relative to the rod. This provides the physician with much more flexibility during surgery, as described in more detail below.

Figure 1:
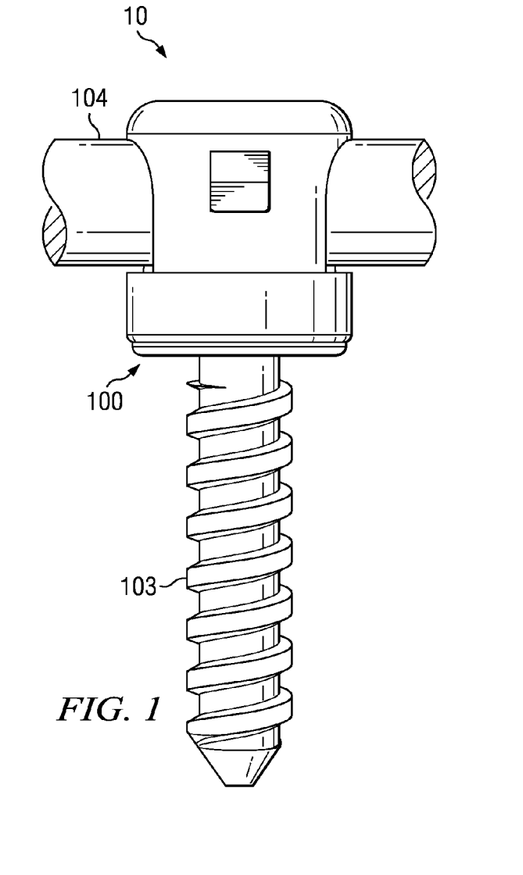
FIG. 1 is a side view of the present invention.

More specifically and referring directly to the figures, FIGS. 1-4 show solid models of the assembly 10. FIG. 1 shows the assembly 10, wherein the screw 103 and rod 104 are inter-connected and locked in place by the body member 100. The assembled screw and rod form a compact structure with the assembly 10.

Figure 2:
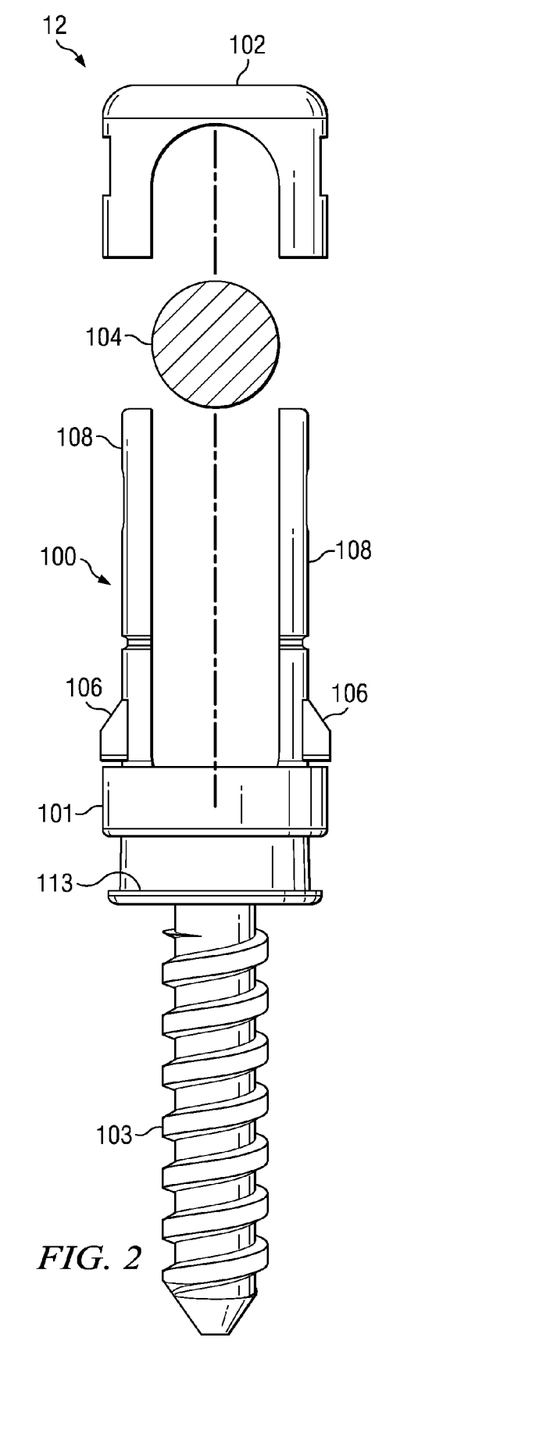
FIG. 2 is an exploded side view of the present invention.
Figure 7:
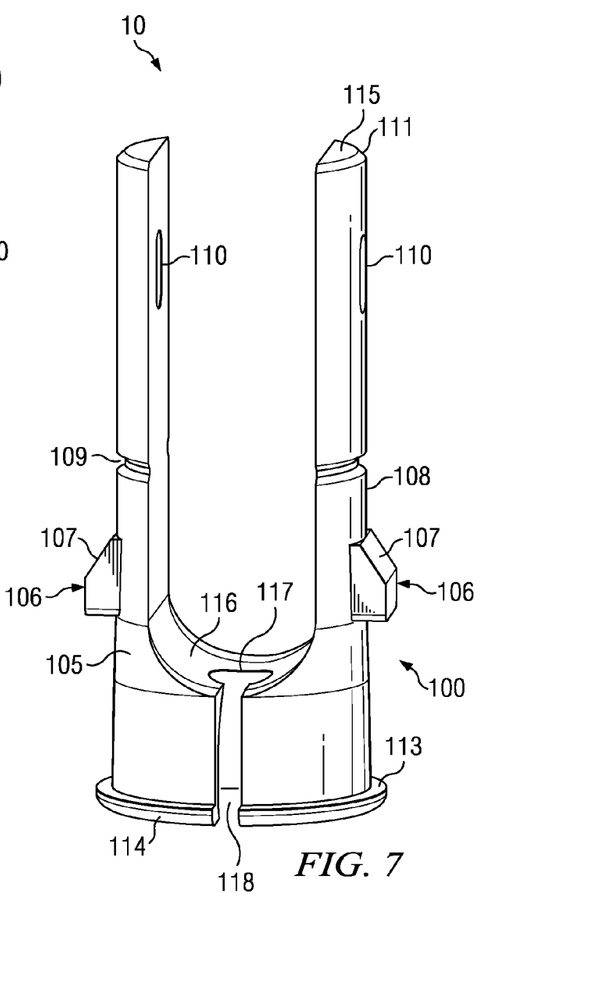
FIG. 7 is a prospective view of the body member of the present invention as shown in FIG. 6 rotated 90°.
Figure 8:
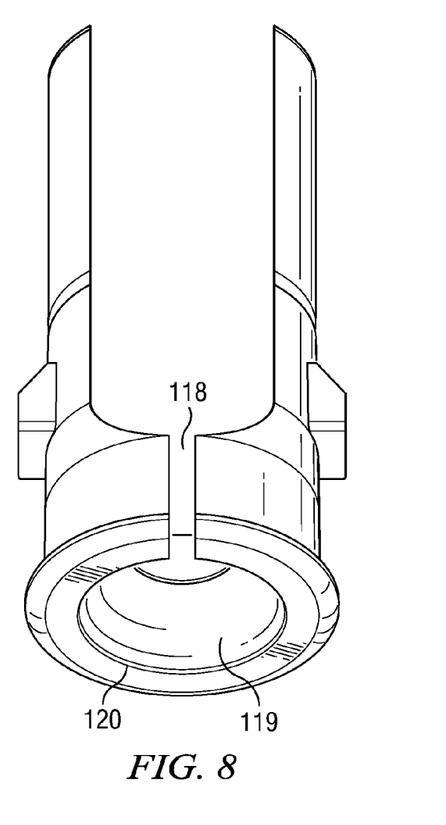
FIG. 8 is a prospective view of the body member specifically showing the screw seat portion.
Figure 9:
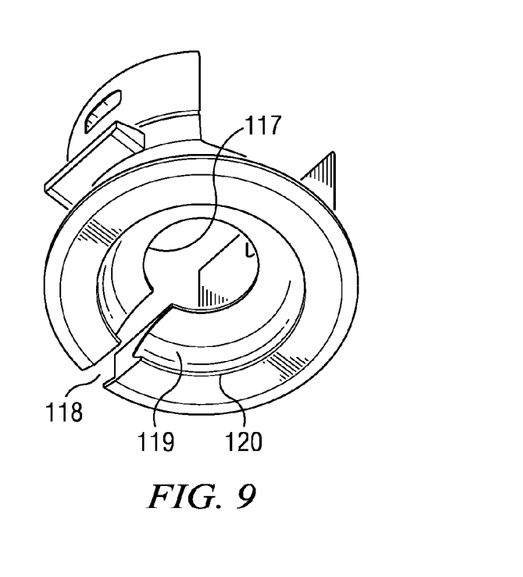
FIG. 9 is a bottom prospective view of the body member showing details of the screw seat.
Figure 10:
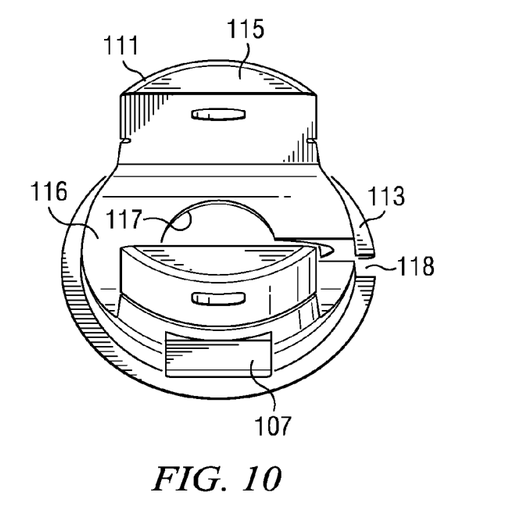
FIG. 10 is a top prospective view of the body member.
Figure 11:
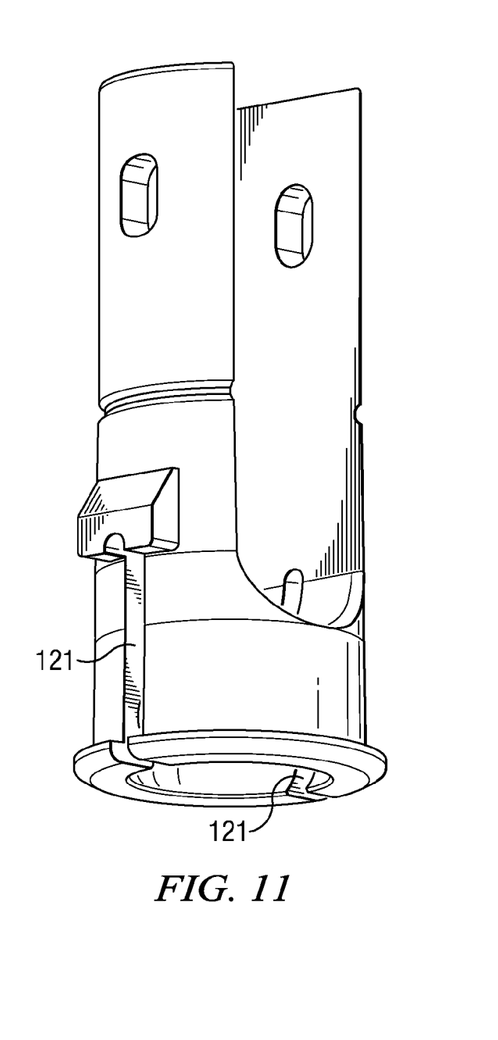
FIG. 11 is a side prospective view of the body member.
Figure 12:
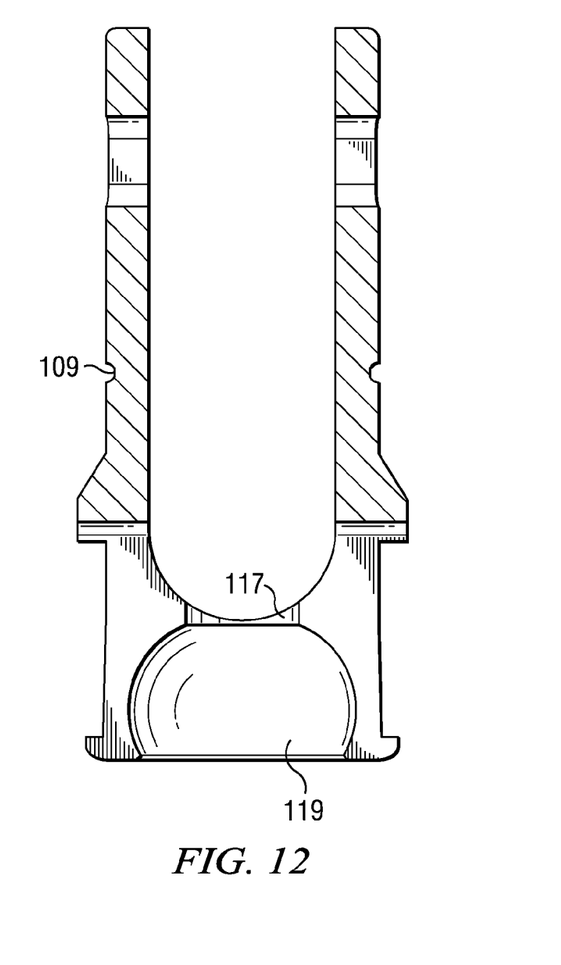
FIG. 12 is a cross-sectional view of the body member.
Figure 13:
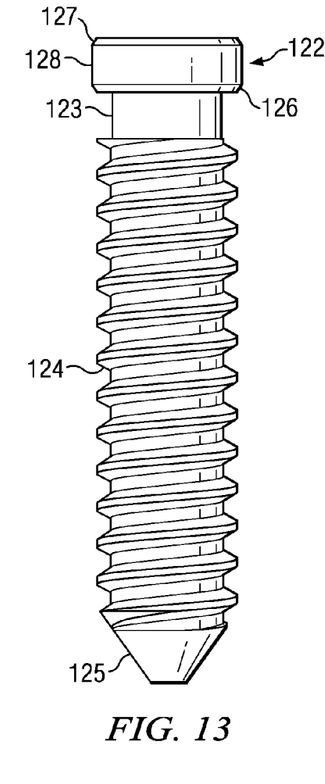
FIG. 13 is a side view of the screw member made in accordance with the present invention.

FIG. 2 shows the polyaxial screw assembly 10 partially assembled and a rod 104 and locking cap 102 disengaged. The locking ring 101 slides over the body member 100 and over side tabs 106 that extend radially outwardly from arm portions 108. The body member 100 includes the arms 108 and a base portion 116, best shown in FIG. 7, defining the rod seat. The arms 108 act as springs allowing the locking ring 101 to radially inwardly push the arms 108. Once in position, the arms 108 spring back elastically. This enables the locking ring 101 to be positioned under the side tabs 106, thereby preventing the locking ring 101 from unintentionally sliding back off of the assembly. A lower lip 113 on the body portion 100 prevents the locking ring 101 from traveling beyond a desired locking point, as described in greater detail below.

Figure 3:
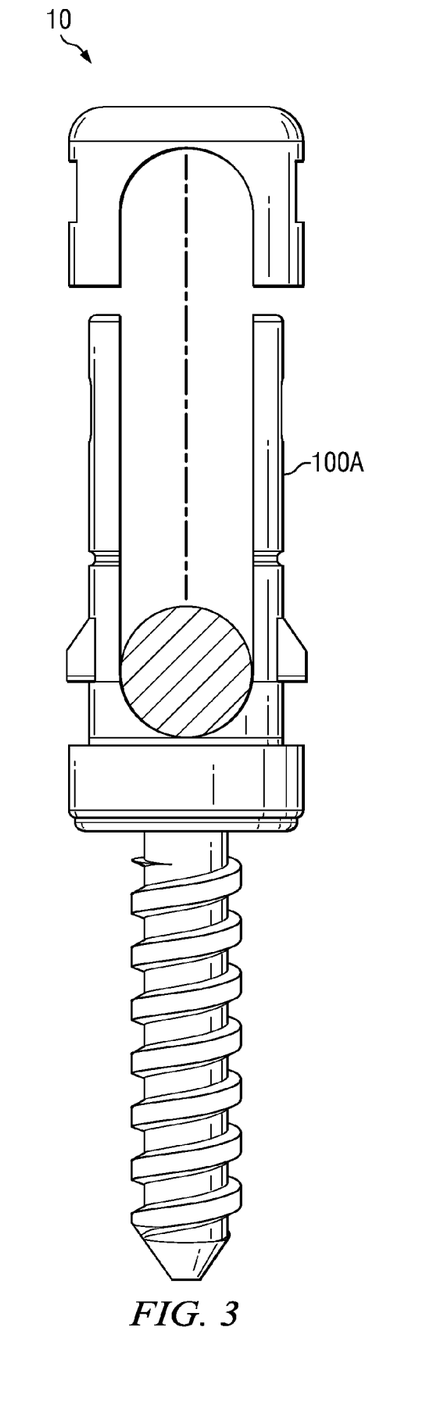
FIG. 3 is a side view of a partially exploded and partially assembled view of the present invention.

The locking ring 101 is in a locked position as shown in FIG. 3. The locking ring 101 is disposed over the outer surface of the screw seat 119 and forced fully down and adjacent to or against the lower lip 113. Based on variation and tolerances, contact with the lip 113 is the maximum locking position. However, it is not necessary for there to be contact with the lip 113 by the locking ring 101 to have a locking action. Rather, the extent that the locking ring 101 is disposed over the screw seat 119 adjustably applies varying degrees of locking force on the screw head.

Once the locking ring 101 is in the locked position, the screw 103 is locked in position relative to the body member 100, thereby preventing rotation of the screw head 122 relative to the body member 100. The bottom portion of the rod 104 is shown to be above the locking ring 101 and not in contact therewith. It is not a restriction of the present invention to have contact or not to have contact between the rod 104 and locking ring 101. However, the locking ring 101 can be adjusted relative to the outer surface of the screw seat 119 to adjust the locking force of the locking ring thereon. This places the screw head 122 in a pre-locking condition wherein a compressing force of the screw seat 119 on the screw head 122 can be adjusted. When some force is exerted on the head of the screw to limit the screw motion, the rod may be pushed against the locking ring, thereby placing it in contact with the locking ring. Full locking can move the locking ring below the bottom of the rod, thus avoiding contact therebetween.

Figure 4:
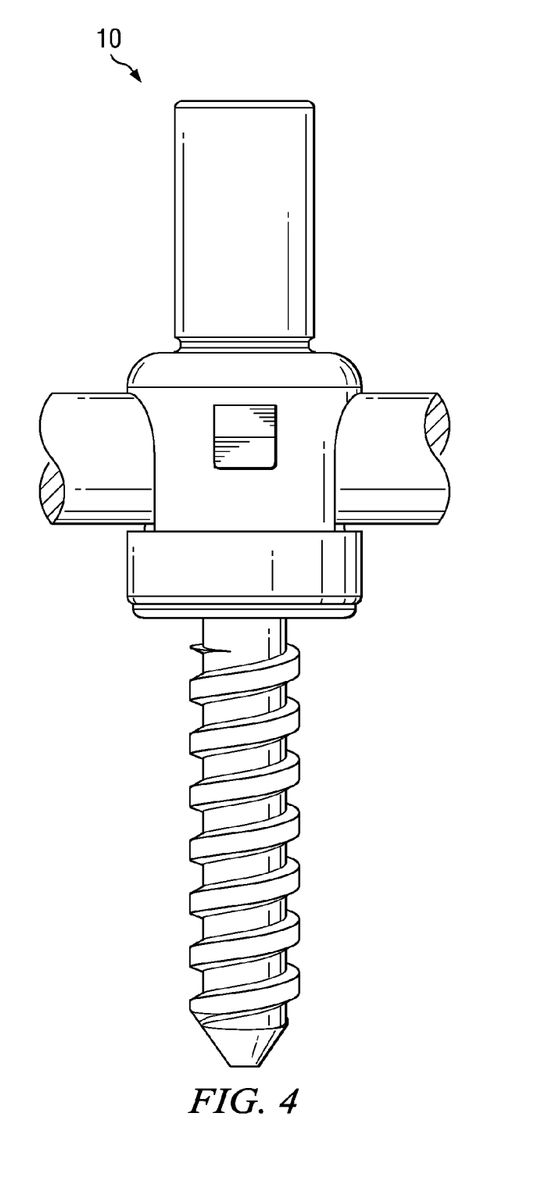
FIG. 4 is a side view of the assembled invention.

FIG. 4 shows the body member 100 including extended tabs 100A, which extend through the central bore of the locking cap 102. The tabs 100A are broken away after locking the rod to the body member, but are included in the preferred embodiment of the present invention to assist and guide the locking cap 102 into a proper position. The extended tabs 100A also assist in introducing and guiding the rod 104 into the rod seat 116. Side tabs 106 extending from arm portion 108 can be biased radially inwardly when the locking cap 102 is pushed downward and return biased radially outwardly into openings 133 in the locking cap 102 to assist in securing the locking cap in a locked condition.

Figure 5:
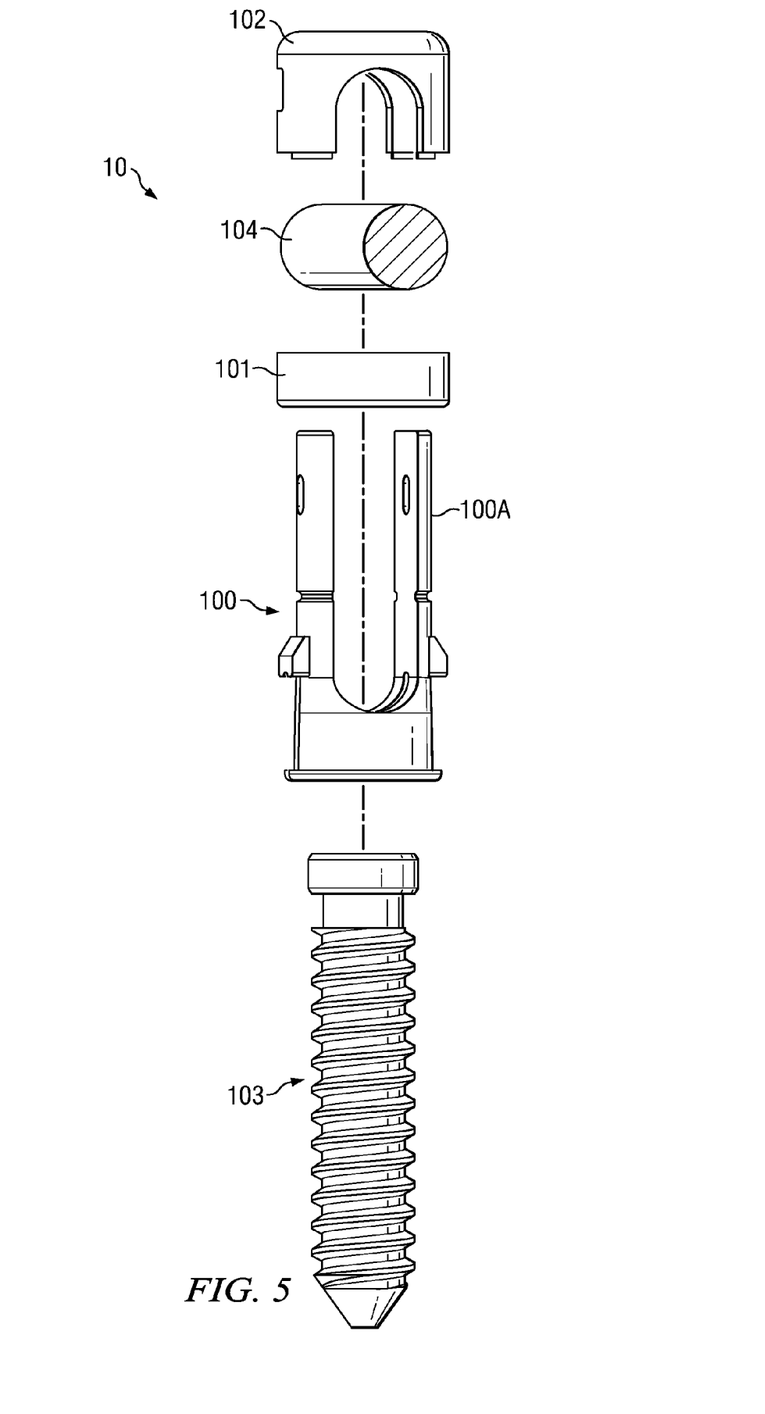
FIG. 5 is a prospective exploded view of the present invention.
Figure 6:
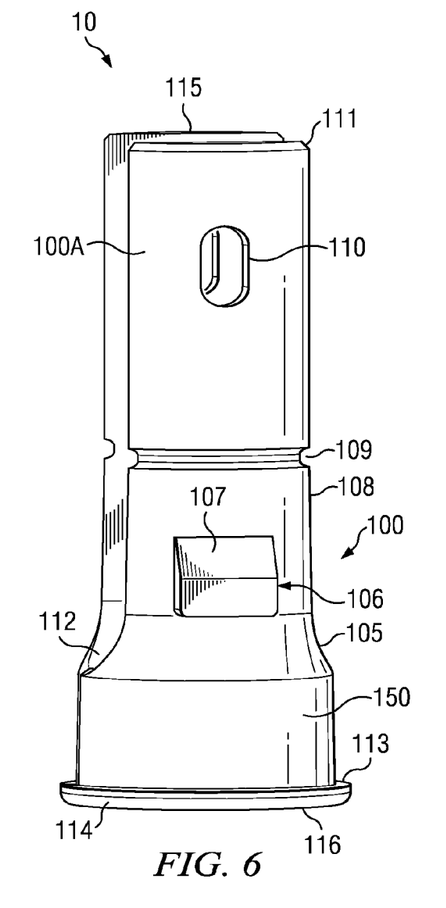
FIG. 6 is a prospective view of the body member of the present invention.

Each of the components of the present invention are shown in FIG. 5. The body member 100 includes the screw seat 119 described above, the head 122 of the screw 103 snapping into the screw seat 119. This allows the screw head to be one size regardless of the thread size of the screw. The locking ring 101 is capable of sliding down over the body member 100 after the head 122 of the screw 103 is in place. After the rod 104 is introduced into the extended tabs 100A and pushed down against the rod seat 116 in the body member 100, the locking cap 102 is disposed over the arms 100A and locked in place as described above.

FIGS. 6-13 show details of the body member 100. The locking ring 101 engages surface 150 of the body member 100, which can be cylindrical or tapered. The locking cap 102 engages arms 108, which can also be cylindrical or tapered. If one of the surfaces is tapered and the other is cylindrical, then a transition zone is created between the two surfaces at 105, which simply allows for a transition of varying diameters in geometry. In addition, the surface 150 can be larger in diameter than the body member 100. In this situation, the transition zone 105 forms a small tapered region. Side tabs 106 extend outwardly from the body member 100, since these tabs 106 are attached to the wall of the body member 100, (defined by the arms 108 and rod seat 116), the remaining wall is thin enough to be elastic, thereby allowing the side tabs 106 to be able to spring inwards and outwards. Raising or lowering the tabs 106 on the arms 108 of the body member 100 relative to the base of the body member 100 changes the stiffness of the spring action.

To allow the locking cap 102 the ability to slide over the side tabs 106 and compress the flexible tab portion, a chamfer or a radius (preferably a chamfer) 107 is machined or formed into the top of the side cap 106. The extended tabs 100A are only present during the placement of the rod 104 into the rod seat 116 and locking of the implant. Once this is accomplished, the tabs 100A are snapped off and removed from the assembly 10. To accomplish this, a groove 109 forms a stress riser such that sufficient pressure on the extended tab 100A will allow the tab 100A to be snapped off of the body member 100. To assist in holding onto the body member 100 during introduction of the rod 104, as well as to provide attachment points for pre-locking and locking of the implant, holes or openings 110 in the extended tabs 100A are provided. To assist the locking cap 102 onto the extended tabs 106, a radius or chamfer 111 is provided in the ends thereof. The top of the extended tabs 105 can be flat, rounded, or any other appropriate form. However, as the locking cap extends above the level of the groove 109, a flat surface is preferred. This prevents any edges of the snapped off portion from being able to contact soft tissue. Accordingly, the body members provided with a first end including the screw seat and a second end including the rod seat.

To allow a curved rod 104 to fully seat within the body member 100, a section of the body member 100 at the bottom of the U-shaped seat is relieved, thereby forming the rod seat 116. A hole 117 allows a screw driver to pass through the polyaxial screw body member 100 into the screw 103 so that the screw 103 can be turned after it is inserted into the body member 100. At least one slot 118 allows the body member 100 to spread sufficiently to allow the screw head 122 to enter into the screw seat 119. Additional slots 121 can be added to provide additional spring to the body member 100 to allow better opening and closing around the screw head 122 during screw head insertion and locking. The screw seat 119 is spherical in shape. A chamfer 120 breaks the edge at the screw seat opening.

To prevent the locking ring 101 from sliding off the body member 100, the lower lip 113 is provided, as discussed above. A blend radius 114 on the lower edge of the lip 113 provides a smooth transition in the case where the implant comes into contact with bone, while the polyaxial screw assembly is being positioned.

Figure 14:
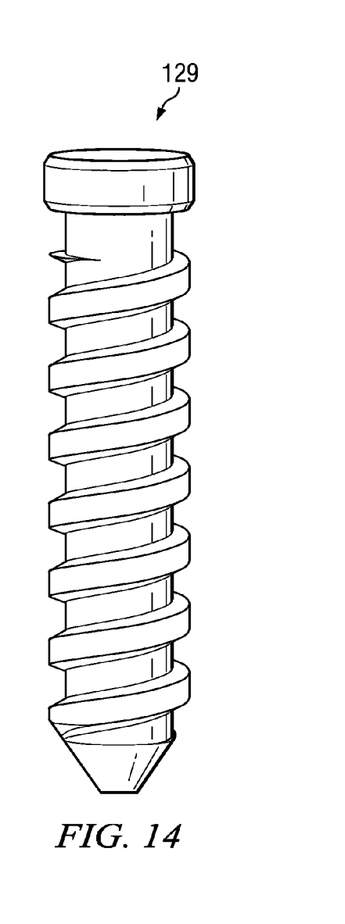
FIG. 14 is a prospective view of the inventive screw.
Figure 15:
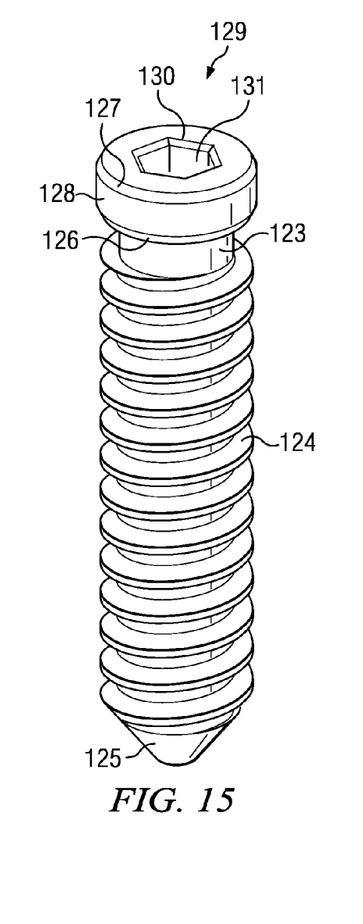
FIG. 15 is a prospective view showing the top portion of the screw member.
Figure 16:
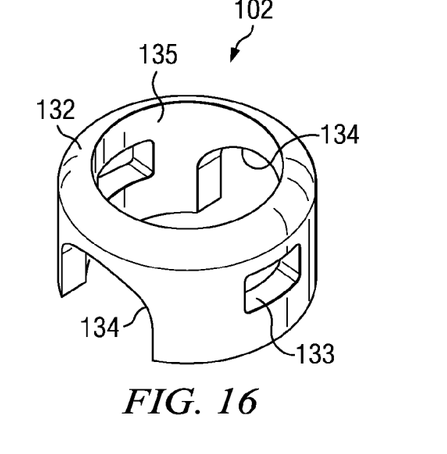
FIG. 16 is a prospective view showing the top portion and side portion of the rod locking member of the present invention.

FIGS. 14-16 show the polyaxial screw 103 of the present invention and various details of its construction. The screw 103 includes a threaded portion 124 for engagement with bone, a neck portion 123, which is generally smooth and cylindrical, and a head section 122. The screw head 122 includes a basically cylindrical shape having an upper tapered portion 127 and a lower tapered portion 126. In FIG. 15, the basic form of the screw head is a diamond or square, depending on the specific measurements of the features of the screw head 122, of which the undesired portions are removed. This creates a very compact head design with two specific regions 126, 127 for contact with the spherical seat 119. The screw 103 includes a tapered end 125, which creates sharp threads at the intersection of the taper and the first few threads. These threads assist in self-tapping or cutting of the threads into the bone during screw insertion. It is common to machine grooves into the tapered tip 125 and/or threads 124 to create additional edges for screw self-tapping.

FIG. 16 shows one method of providing a feature for allowing a screw driver to connect with the screw 103. In the top surface of the screw 129, a hexagon is machined into the surface 131 to a sufficient depth to thereby allow a screw driver to engage the hexagon and not slip out. A chamfer 130 aids in guiding the screw driver into the screw head hexagon.

Figure 17:
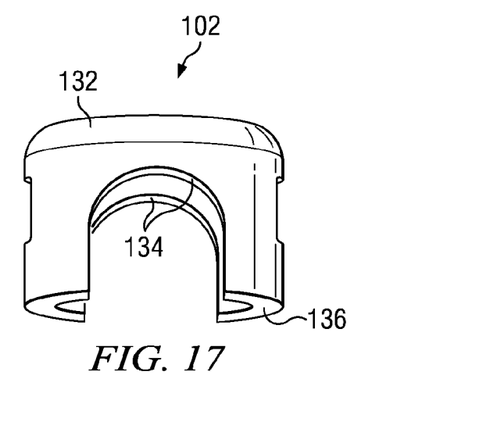
FIG. 17 is a side prospective view of the rod locking member.
Figure 18:
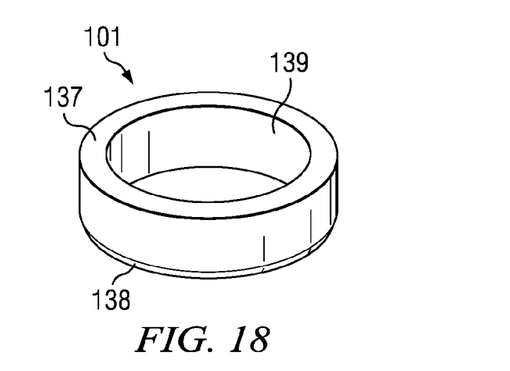
FIG. 18 is a prospective view of the locking ring of the present invention.

The locking cap 102 is shown in FIGS. 17 and 18 and includes a cylindrical portion having an internal bore or hole 135. This bore 135 can be cynlindrical or tapered. U-shaped slots 134 are cut into the side of the locking cap 102, thereby allowing the locking cap to clear the rod 104. To secure the locking cap 102 as well as provide for additional positive locking to the body member 100, slots or holes 133 are provided. These slots or holes 133 provide sufficient clearance to allow the side tabs 106 to slide into the slots or holes 133. A radius 132 on the top of the locking cap 102 provides a smooth surface for tissue contact.

Figure 19:
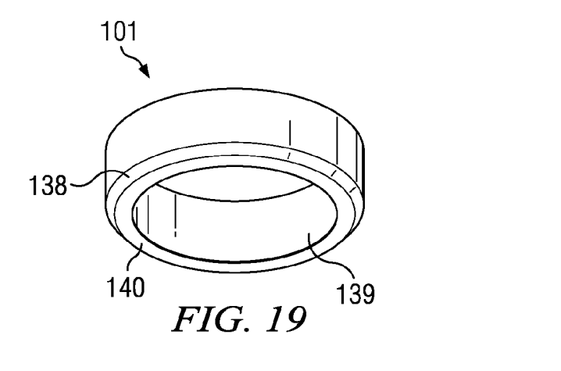
FIG. 19 is a prospective view showing an opposite surface of the locking ring shown in FIG. 18.
Figure 20:
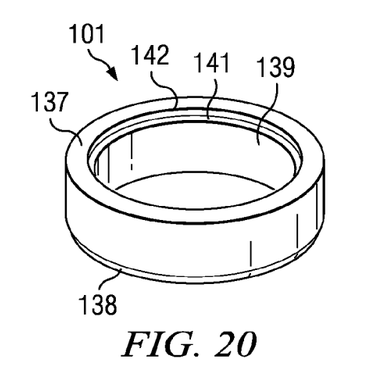
FIG. 20 is a prospective view of a second embodiment of the locking ring made in accordance with the present invention.

The polyaxial screw locking ring 102, shown in FIG. 19, includes a cylindrical ring shape having an internal bore 139, which can be a straight cylindrical bore or a tapered bore. The top surface of the locking ring 137 is designed to contact the lower edge of the locking cap 136 during assembly locking. It is possible to lock the rod and screw with the body member without the two components touching, since both locking means are independent. However, it is preferable to have contact such that when the locking cap 102 is placed on the body member 100, the locking cap 102 pushes the locking ring 101 into the proper locking position. To avoid any sharp edges in contact with the bone when the locking ring 101 is in the fully locked position, a radius 138 is provided to smooth the edge. This edge could alternatively be chamfered. The bottom 140 of the locking ring 101, in maximum locking position, can contact the lip 113, as described above. It is not necessary for this to occur to have maximum locking of all components.

Figure 21:
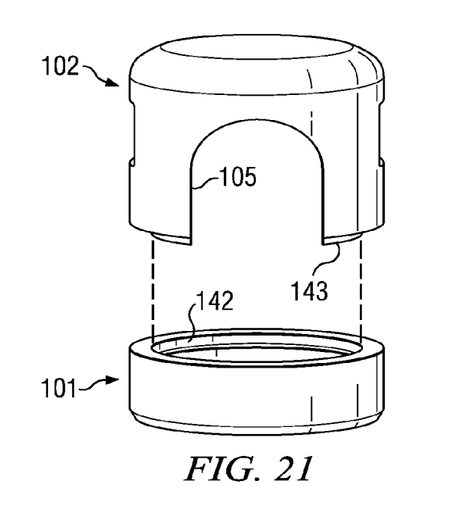
FIG. 21 is a side view of the rod locking member and locking ring of the present invention.
Figure 22:
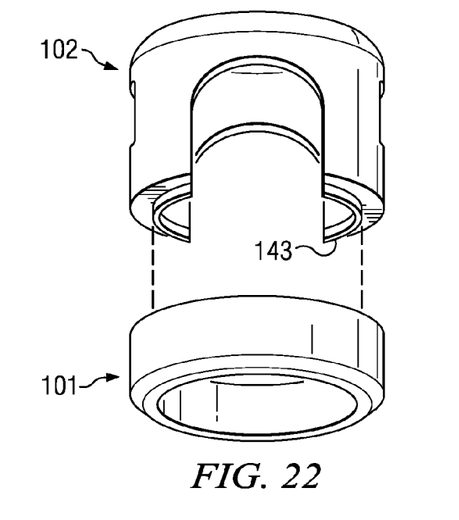
FIG. 22 is a prospective view showing the bottom surfaces of the rod locking member and locking ring of the present invention.
Figure 23:
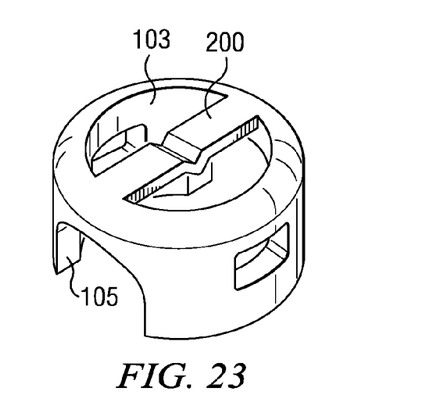
FIG. 23 shows an alternative embodiment of the rod locking member.

It is also possible to have an alternative structure of the locking ring 101 such that a portion of the locking cap 102 engages more directly with the locking ring 101. FIG. 21 shows a groove machined or formed into the internal bore 39. This groove 142 having a bore larger than the internal bore 139, creates a ledge 141. As shown in FIGS. 22 and 23, the lower surface of the locking cap 102 includes a corresponding feature 143 to fit in mating contact with the groove 142 within the locking ring. During locking, the small extension 143 slides within the groove 142 and the locking ring. This prevents the lower portion of the locking cap 102 from flexing outwardly, as the arms on each side of the u-shaped rod seat is held by the extension and groove arrangement. It is also possible to accomplish this function through other means, such as having the lower surface of the locking cap tapered, such that the smaller end of the taper extends in the direction of the locking ring. The locking ring would then have a corresponding tapered feature, such that when the two components contact each other, the male taper of the locking cap would engage the female taper of the locking ring, thereby creating the same effect of the radially extending lip.

Figure 24:
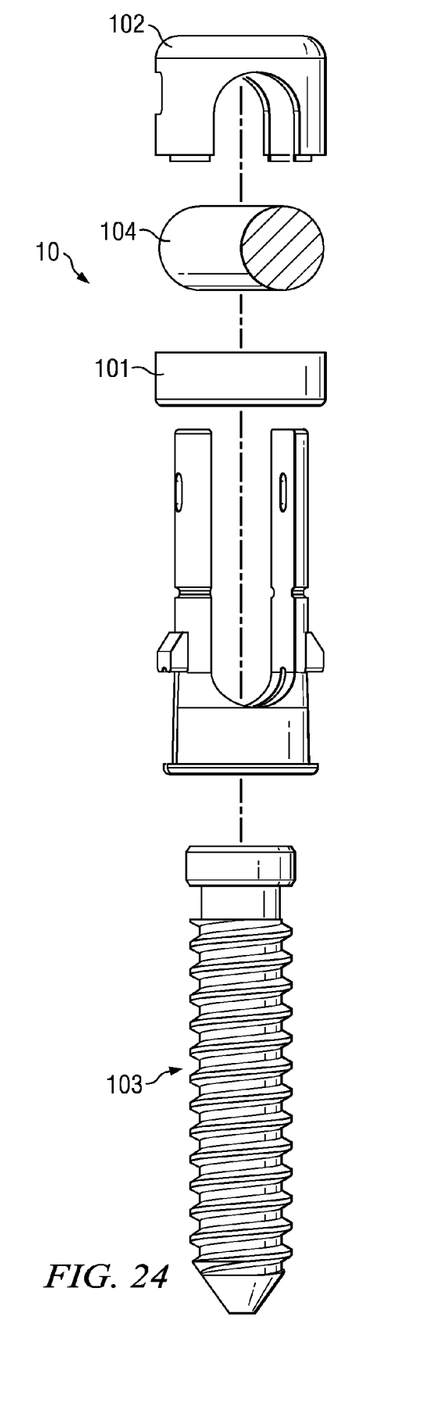
FIG. 24 is an exploded side view of the assembly made in accordance with the present invention.
Figure 25:
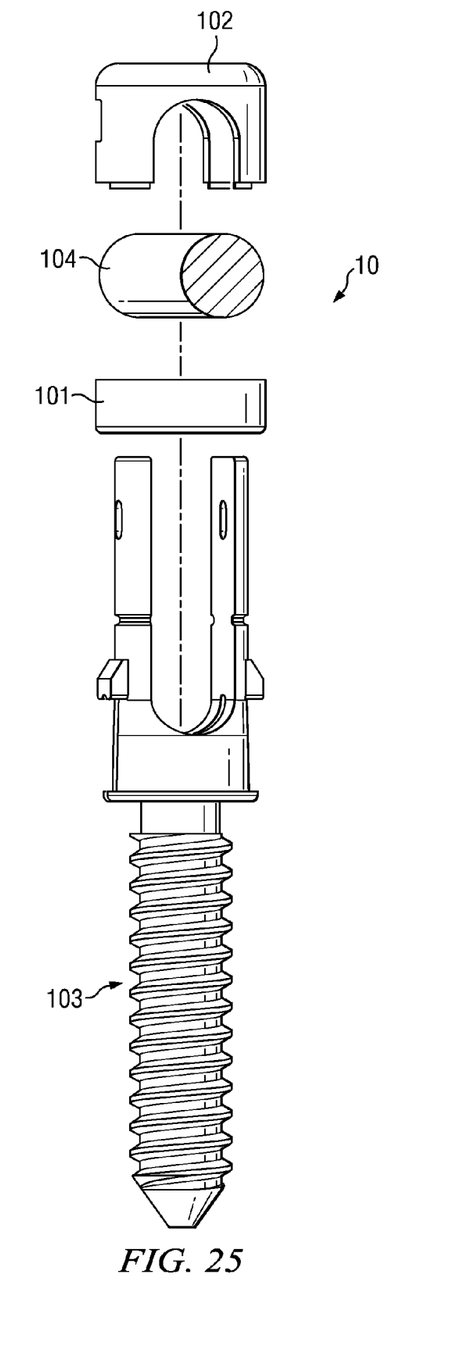
FIG. 25 is a partially assembled side view of the present invention.
Figure 26:
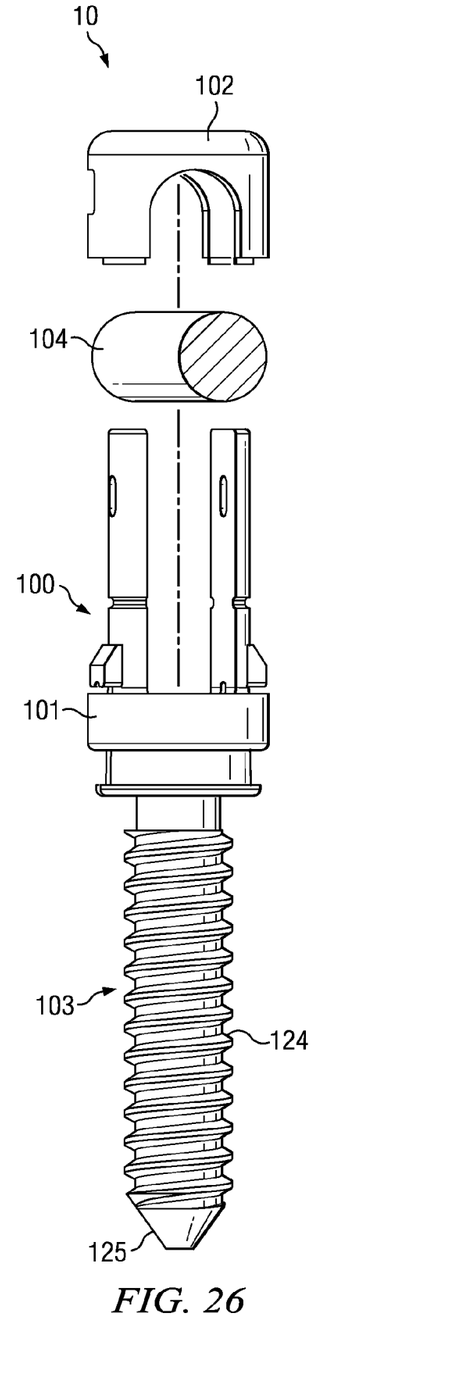
FIG. 26 is a further assembled side view of the present invention.
Figure 27:
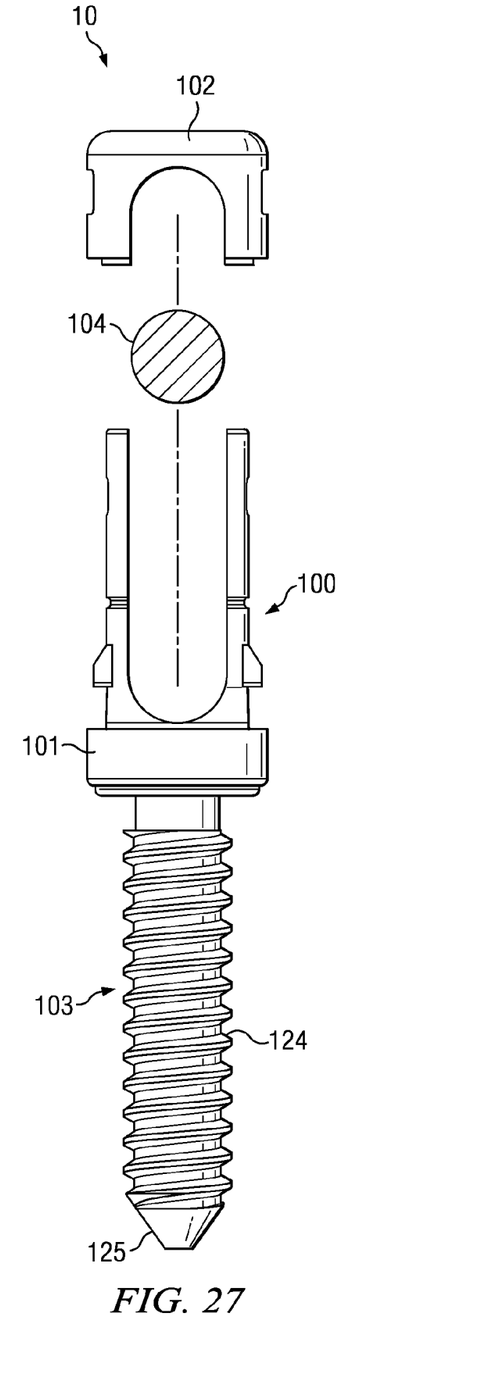
FIG. 27 is a side view of a partially assembled assembly made in accordance with the present invention.

FIGS. 24 and 25 show the assembly drawings of the polyaxial screw 103. It is possible to insert the screw 103 into the body member 100 prior to surgery and the remainder of the components added after, or with the screw already inserted into the polyaxial body member 100. When the polyaxial body member 100 and screw 103 are provided assembled, it is preferable to also have the locking ring 101 in the unlocked position already disposed on the body member 100. This simplifies the implant for the surgeon, as the rod 104 and the locking cap 102 are the only components that need to be introduced after the screw assembly is attached to the bone. FIG. 26 shows the assembly with the locking ring 101 in the unlocked position. This allows the screw head 122 to pivot freely. FIG. 27 shows the locking ring 101 in the fully locked position, which prevents screw head rotation.

The above-described assembly provides a body member 100 including a U-shaped slot defining the rod seat for accepting the rod 104 and the spherical screw seat 119 for accepting the screw head 122 of the screw 103. By using a predominantly cylindrical screw head 122 cut from a diamond or square shaped as described above, the overall height of the assembly 10 can be significantly reduced without comprising and possibly improving screw head locking. The reasoning behind this is the problem of the minimal contact of the standard prior art spherical screw head in a spherical seat. No matter how precise the machining of the screw head and the spherical seat, the two are never exactly the same. Thus, a gap exists between the two except at very specific locations, which represent only a fraction of the surface area of the screw head. By utilizing the diamond shape of the present invention with the points cut off, a cylinder is formed having two chamfers. The chamfers are matched closely to an angled tangent of the circle defined by the spherical screw head seat. This creates a flat surface within the ark, but is fairly close to matching since the overall contact area is relatively small. This design provides for four edges to further enhance engagement with the spherical wall of the screw head seat. It is also possible to use a curvate surface in place of the chamfer to still create a relative edge. This curvate surface need not be spherical in an attempt to match the sphere of the screw head seat, but can be a portion of an oval as well. The smaller the chamfered or curvate surface is, the sharper the edge contact between the screw and the body member spherical seat. Since rotation of the screw head within the seat of the body is a key part of the design, the ideal balance of smooth rotation and sufficient locking is created by allowing sufficient distance between the two circular lines of contact at the top and bottom of the cylindrical screw head. An alternative implant option is effectively creating a tapered surface that the diamond shape is sharper towards one side. Therefore, it is not necessary that the chamfers on the top and bottom of the cylinder be equal to achieve locking.

The screw seat including the slots therein allows sufficient flexibility for the screw 103 to enter from the bottom of the body member 100. Entering from the bottom of the body member 100 avoids restrictions on what diameter screw thread can be used without having to create a two-part screw where the head is separate from thread and mechanically attaching them together after the head is inserted into the body member. Thus, any major thread diameter is possible.

The present invention also addresses another issue, wherein the implant assembly rotates freely such that holding the implant rod in the desired position without a screw assembly rotating is very difficult in situ. By utilizing a screw head 122 that is large enough to interfere and contact the spherical seat 119 of the present invention, sufficient friction can be created between the screw head 122 and the screw seat 119 to hold the screw head 122 in position while still allowing the surgeon the ability to rotate the body member 100 relative to the screw 103 as needed. This greatly assists in alignment of the rod seat 116 with the rod 104. In addition, and more significantly, interference between the screw head 122 and the spherical seat 119, spreads the outer surface of the screw seat by opening at the slots. This in effect creates a radially outwardly extending taper on the outside of the lower portion of the body member without having the machine into the body member.

As described above, the locking ring 101 is basically a cylinder designed to slide over the body member and compress the outer surface of the screw seat against the screw head in order to lock the screw head seat in place. The cylinder of the locking ring has an internal bore, which can have a straight cylindrical wall, which is easier to machine and measure than a small tapered wall. As there is already a taper created on the outer surface of the screw head seat due to the interference of the screw head with the spherical seat, there is no need to taper the inner aspect of the locking ring. By pressing the locking ring 101 down and over the outer aspect of the spherical screw seat, the locking ring 101 engages the created taper, thereby compressing the spherical seat against the screw head to securely lock the screw 103 in the desired position. As described above, the locking ring 101 can be adjusted to adjust the locking force. This adjustment can be done totally independent of the application and locking of the locking cap 102 over the rod 104.

The section of the arm 108 below the extended tabs 106 are relatively thin in cross-section and are thereby quite flexible. By placing side tabs that extend outwardly from the arms, the arms can be used as a spring to allow the side tabs to easily move inward and outward. The locking cap 102 can slide over the arms and the flexible nature of the arms allow the side tabs to flex inwardly and then outwardly to engage slots or holes 133 in the locking cap. These features can be inversed, such that the body member includes holes or slots and the locking cap includes tabs or pins. Also, the flexibility of the arms is relative to the length of the moment arm, such that less force is required to push the side tab inward, the farther it is away from the bottom rod seat 116 of the u-shaped channel.

The locking cap 102 is basically a ring having an internal bore 103 as shown in FIGS. 21 and 23. The cap 102 includes U-shaped openings 105 being disposed about the rod 104 and grooves or slots to slide and fit over the side tabs of the body member 100. As described above, this can be varied by allowing the slots to change the pins or tabs and the body features were inversed. The internal bore can be straight or tapered. However, by allowing interference with the rod, the arms of the U-shaped slot will naturally move outwardly creating a taper. By using a chamfer at the top of the arm just below the snap off point, the spread arms have a feature to allow the locking cap to slide onto the arms, which without the chamfer would be spread larger than the diameter of the locking cap. By pressing the locking cap downwardly, the arms compress around the rod, thereby securely locking it into position. In addition, the locking cap can include a central clip 200 that can be used to provide additional force against the rod. This locking clip is sufficiently flexible to compensate for contoured rods.

Overall, the present invention allows for independent locking of the rod and screw. By locking the locking ring 101 into the locking position, the screw head is fixed. However, without the locking cap in place, a rod 104 is free to move relative thereto. This is an extremely helpful feature in certain surgical procedures, wherein screw head rotation would not be desirable. It also allows a polyaxial screw to work as if it is a fixed screw. The locking ring 101 can also be used to increase friction against the screw head without fully locking the screw head by not pressing it downward into its final locking position.

The locking cap 102 possesses the same function of adjustability in that force can be applied against the rod 104 without fully locking the rod 104 in position. As the locking cap 102 engages the arms 108 of the U-shaped slot in the body member 100, forces apply to the rod 104. The further the locking cap 102 moves towards the final locking position, the more force is applied against the rod 104. The body member 100 can also be provided more than one side tab, thereby forming a ratchet effect, such that varying locking loads to the rod 104 control than better moderated by the surgeon, yet still locked in those positions.

In view of the above, the present invention provides a method of fixing a rod to a screw by inserting a screw head into a screw seat in one end of a body member, inserting a rod into a rod seat in a second end of the body member, and then selectively and independently adjusting a locking force on both the screw head and rod within the screw seat, respectively. More specifically, the screw head is inserted into the screw seat and a locking ring is disposed about the body portion and space from the outer surface of the screw seat prior to surgery. The rod is inserted within the rod seat and independently and selectively locking forces apply to the locking ring about the screw seat and the rod locking cap member about an outer surface of the rod seat during surgery.

The present invention further provides the method of fixing the rod to the screw head by seating the screw head having multiple contact points in a screw seat of a body portion causing the screw head to interfere with and contact multiple portions of the spherical seat creating sufficient friction to lock the screw head in a desired position during rod insertion while also allowing the body portion to rotate relative to the screw head.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains. The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

The invention claimed is:

1. A screw and rod fixation assembly, comprising:
 a body member including:
  a screw seat:
   having internal walls shaped to seat a screw head therein;
   having a maximum internal diameter; and
   defining a screw head opening having a diameter less than the maximum internal diameter;
  a cylindrical outer surface disposed at least partially about the screw seat, the cylindrical outer surface having at least one slot shaped to permit flexing of the cylindrical outer surface; and
  a rod seat shaped to seat a rod therein opposite the screw seat; and
 a screw having a head with a maximum outer diameter larger than the maximum internal diameter such that, when the head of the screw is inserted through the screw head opening and into the screw seat, the internal walls of the screw seat frictionally interfere with the head and force a portion of the cylindrical outer surface to flex outward and change a portion of the cylindrical outer surface into a tapered outer surface section.

2. The assembly according to claim 1, further comprising an adjustable locking ring having an internal wall with a diameter sufficient to slide over the cylindrical outer surface when the portion of the cylindrical outer surface is not flexed outward and, when the portion of the cylindrical outer surface is flexed outward, the internal wall engages the tapered portion of the cylindrical outer surface to adjustably apply an inwardly directed and increasing force to the head contained within the screw seat as the locking ring is forced further along the flexed outward portion of the cylindrical outer surface.

3. The assembly according to claim 1, further comprising an adjustable rod locking member that removably connects to the rod seat and adjustably applies an inwardly directed locking force against a rod seated in the rod seat.

4. The assembly according to claim 3, wherein:
 the rod seat includes:
  a base portion adjacent one end of the cylindrical outer surface; and
  two opposing spaced-apart arms extending from the base portion to define a rod pocket therebetween to seat a rod therein; and
 the rod locking member has a compression device adjustably and selectively compressing the two arms about a rod seated in the rod pocket to, thereby, adjustably and selectively lock the rod in the rod pocket.

5. The assembly according to claim 4, wherein:
 the two arms:
  are outwardly flexible to allow outward deflection of the arms when the rod is seated therebetween; and
  have opposing outer surfaces that, together, define an outer arm diameter from a distance between the opposing outer surfaces of the arms; and
 the compression device of the rod locking member has an annular body portion defining an internal bore shaped to receive and retain the two arms therein, the internal bore has a bore diameter smaller than the outer arm diameter such that, when the internal bore is applied about the two arms, the two arms selectively radially inwardly deflect to adjustably grip and lock the rod seated within the rod pocket.

6. The assembly according to claim 5, further comprising a fixing device that fixedly locks the rod locking member with the rod seated in the rod pocket.

7. The assembly according to claim 5, wherein:
each of the two arms has a radially outwardly extending projection; and
the rod locking member defines corresponding recesses positioned to engage with a respective projection such that, when the projections are respectively engaged with the recesses, the rod locking member locks the rod within the rod pocket.

8. The assembly according to claim 5, wherein:
the rod locking member has radially inwardly extending projections; and
each of the two arms defines a radial recess that is positioned to engage with a respective one of the projections such that, when each of the projections is respectively engaged with the radial recess, the rod locking member locks the rod within the rod pocket.

9. The assembly according to claim 1, wherein the screw seat is a substantially spherical screw seat.

10. The assembly according to claim 1, wherein the screw seat is an ovoid screw seat.

11. The assembly according to claim 1, wherein flexing of the cylindrical outer surface causes a change in shape of the screw seat.

12. The assembly according to claim 1, wherein the rod seat has a substantively spherical inner surface.

13. A screw and rod fixation assembly, comprising:
a body member including:
a screw seat:
having internal walls shaped to seat a screw head therein;
having a maximum internal diameter; and
defining a screw head opening having a diameter less than the maximum internal diameter;
a cylindrical outer surface disposed at least partially about the screw seat, the cylindrical outer surface having at least one slot shaped to permit flexing of the cylindrical outer surface; and
a rod seat shaped to seat a rod therein opposite the screw seat;
a screw having a head with a maximum outer diameter larger than the maximum internal diameter such that, when the head of the screw is inserted through the screw head opening and into the screw seat, the internal walls of the screw seat frictionally interfere with the head and force a portion of the cylindrical outer surface to flex outward and change a portion of the cylindrical outer surface into a tapered outer surface section;
an adjustable locking ring having an internal wall with a diameter sufficient to slide over the cylindrical outer surface when the portion of the cylindrical outer surface is not flexed outward and, when the portion of the cylindrical outer surface is flexed outward, the internal wall engages the tapered portion of the cylindrical outer surface to adjustably apply an inwardly directed and increasing force to the head contained within the screw seat as the locking ring is forced further along the flexed outward portion of the cylindrical outer surface; and
an adjustable rod locking member that removably connects to the rod seat and adjustably applies an inwardly directed locking force against the rod seated in the rod seat.

* * * * *